United States Patent [19]

Schwengers et al.

[11] Patent Number: 4,910,142
[45] Date of Patent: Mar. 20, 1990

[54] CELL CULTURE MICROCARRIER, METHOD FOR PREPARING SAME AND USE THEREOF FOR CULTIVATING ANCHORAGE-DEPENDENT CELLS

[75] Inventors: Dieter Schwengers, Dormangen; Ingrid Keller, Mönchengladbach, both of Fed. Rep. of Germany

[73] Assignee: Pfeifer & Langen, Cologne, Fed. Rep. of Germany

[21] Appl. No.: 293,197

[22] Filed: Jan. 4, 1989

Related U.S. Application Data

[62] Division of Ser. No. 691,006, Jan. 14, 1985, Pat. No. 4,824,946.

[30] Foreign Application Priority Data

Jan. 28, 1984 [DE] Fed. Rep. of Germany ....... 3402927

[51] Int. Cl.$^4$ ............ C12N 5/00; C08B 37/02
[52] U.S. Cl. .......... 435/240.24; 435/240.23; 435/240.243; 435/178; 536/55.1; 536/112
[58] Field of Search ............. 435/178, 240.23, 240.24, 435/240.243; 536/55.1, 112, 123

[56] References Cited

U.S. PATENT DOCUMENTS

| | | | |
|---|---|---|---|
| 3,910,819 | 10/1975 | Rembaum et al. .............. | 195/1.7 |
| 4,293,654 | 10/1981 | Levine et al. ................ | 536/51 |
| 4,415,668 | 11/1983 | Siegel ......................... | 435/240.24 |
| 4,504,547 | 3/1985 | Horodniceanu et al. .... | 435/240.243 |
| 4,591,638 | 5/1986 | Ahrgren et al. ............. | 536/112 |
| 4,661,407 | 4/1987 | Henderson ................... | 435/240.24 |

FOREIGN PATENT DOCUMENTS

| | | | |
|---|---|---|---|
| 1197842 | 12/1985 | Canada ........................ | 536/51 |
| 0046681 | 3/1982 | European Pat. Off. ....... | 435/240.24 |
| 0066135 | 12/1982 | European Pat. Off. . | |
| 0066726 | 12/1982 | European Pat. Off. ....... | 435/240.24 |
| 53-105584 | 9/1978 | Japan ........................... | 536/112 |
| 63-209582 | 8/1988 | Japan ........................... | 435/240.24 |
| 63-237782 | 10/1988 | Japan ........................... | 435/240.24 |
| 2059991 | 4/1981 | United Kingdom .......... | 435/240.24 |
| 8503520 | 8/1985 | World Int. Prop. O. .... | 435/240.243 |
| 8505375 | 12/1985 | World Int. Prop. O. ...... | 435/240.24 |

OTHER PUBLICATIONS

Levine et al.; Chemical Abstracts 93:3451d (1980).
"Recent Developments in Microcarrier Cell Culture", J. Clark et al., Presentation from Biotech 1983; London, May 4-6, 1983, Pharmacia Fine Chemicals, Sweden.

*Primary Examiner*—Ronald W. Griffin
*Assistant Examiner*—Nancy S. Carson
*Attorney, Agent, or Firm*—Wegner & Bretschneider

[57] ABSTRACT

A cell culture microcarrier having positively charged cross-linked polysaccharides and basic groups linked therewith wherein the basic groups have the formula (I)

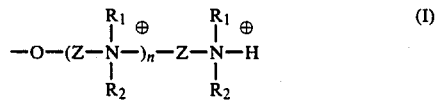

with

Z being an optionally substituted hydrocarbon chain having at least 2 carbon atoms,
$R_1$ and $R_2$ being the same or different and representing alkyl, aryl, or aralkyl groups, and
n is at least 1.

4 Claims, 2 Drawing Sheets

CELL CULTURE MICROCARRIER, METHOD FOR PREPARING SAME AND USE THEREOF FOR CULTIVATING ANCHORAGE-DEPENDENT CELLS

This application is a divisional application of Ser. No. 691,006 filed Jan. 14, 1985, now U.S. Pat. No. 4,824,946.

The present invention relates to a cell culture microcarrier having positively charged chemical portions comprising cross-linked polysaccharides and basic groups linked therewith, a method for preparing same, and the use thereof for cultivating anchorage-dependent cells in a microcarrier culture.

BACKGROUND OF THE INVENTION

The fundamentals of maintaining and augmenting human and animal cells in cell cultures have been systematically developed during the last twenty years. Methods for cultivating cells have now been firmly established for the production of vaccine substances, antibodies, interferon, enzymes, and hormones in many laboratories.

Primary cells and diploid cells require a solid substrate having a distinct surface charge for their growth. These cells are designated as "anchorage-dependent" cells since they are only able to grow if they can adhere to a carrier.

Initially, glass in the form of Petri dishes, culture bottles, or roll-culture flasks was used as the carrier. However, there can be formed only a monolayer on the surfaces of the equipment so that the surface available per unit will be limited. Thus, for such cell augmentation cultures on a commercial scale, thousands of roll-culture flasks have to be cleaned, sterilized, filled with nutrient medium, inoculated with cells, and harvested once the cell augmentation is finished. Since all of these steps have to be carried out under sterile conditions, they are very labor- and cost-intensive.

DISCUSSION OF THE PRIOR ART

By the introduction of the cell culture augmentation on microcarriers by A. L. van Wezel, Nature 216 (1967), p. 64, an improved technology has been developed that could be suitable to eliminate the described problems. In this technique, microcarriers having an average particle size in the range from 100 to 300 $\mu$m are suspended in a nutrient medium. In as far as the microcarriers have a suitable surface charge, the anchoragedependent cells will adhere to the microcarriers and grow thereon. Two to 5 g/l (dry weight) of microcarrier provide a surface in the nutrient medium of from 0.76 to 1.9 m$^2$/l of culture volume. In contrast, the largest roller flasks will only provide a surface of about 0.16 m$^2$. Thus, 1 l of a culture containing microcarriers will be able to replace from 5 to 12 large roller flasks. However, on the commercial scale, microcarriers so far have not yet gained the importance having been expected, since the microcarriers as so far developed still have a number of inherent drawbacks.

A.L. van Wezel originally used insoluble dextran beads substituted with diethylaminoethyl groups and commercially available as DEAE Sephadex A-50 (Pharmacia AB, Sweden). However, in the course of the use thereof, cytotoxic and nutrient adsorption effects appeared, manifested by an initial death of cells and an unsatisfactory cell growth; cf. C.-B. Horng, W. Melimaus (Biotechnology and Bioengineering, Vol. 17 (1975), pp. 715–732). In the meantime, various improvements for microcarriers have been developed, which are capable of eliminating some of the original disadvantages. Thus, in the German Offenlegungsschrift 29 09 340 there has been described a process for pre-treating microcarriers for cell cultures wherein the beads are impregnated with fetal calf serum and heated in the serum at 75° C. to 90° C. for about 10 minutes.

Levine, Wong, Wang and Thilly experimented with microcarriers of various charge densities and concluded that DEAE dextran beads having a diameter of 150 $\mu$m and a charge density of 2 meq/g of the dry dextran matrix constitute the optimum characteristics for the adhesion of the cells and the growth thereof; cf. D. F. Levine et al., Somatic Cell Genetics, Vol. 3 (1977), pp. 149–155; U.S. Pat. No. 4,189,534 and German Offenlegungsschrift No. 27 49 989.

Microcarriers that contain a charge density of only 1.5 to 2.0 meq/g instead of 5.4 meq/g, in the meantime, have been marketed by the firm Pharmacia AB under the designation "Cytodex 1"and by the firm Flow Laboratories under the designation "Superbeads". A survey of the properties and possible applications of these products and an introduction into the development of the microcarrier technology is presented by the company brochure "Microcarrier Cell Culture, Principles & Methods", edition 1981, available from the firm Pharmacia AB, Uppsala, Sweden.

Unfortunately, there has been shown that even these improved microcarriers having a significantly reduced charge density, in practice, still display cytotoxic effects, particularly with sensitive cells.

The European Offenlegungsschrift (Published Unexamined Patent Application) No. 0 066 726 premises that these cytotoxic properties of the microcarriers based on DEAE dextran reside in the chemical structures of the microcarriers themselves. Thus, it has been known that DEAE microcarriers, in addition to the DEAE substituent comprising a tertiarily bonded nitrogen, also contain groups comprising a quaternarily bonded nitrogen, which latter groups are formed in the synthesis of the microcarriers by a further reaction with more chloroethyl-diethylamine, a reaction which never can be completely avoided. These so-called "tandem groups" are supposed to have an alkylating action and to be toxic; cf. L. Ahlgren et al., "Polymeric Amines and Ammonium Salts", E.J. Goethals, Pergamon Press, pp. 293–294. In the company brochure "Microcarrier Cell Culture, Principles & Methods" by Pharmacia AB, at page 27, there has further been mentioned that, in the known preparation procedures for DEAE dextran microcarriers, up to 35% of tandem groups are formed. In the product Cytodex 1, the tandem group content is reduced to about 15%.

In order to completely exclude the aforementioned cytotoxic effect, there have been described in European Offenlegungsschrift 0 066 726 microcarriers that only contain quaternary amino groups. Such microcarriers have been marketed under the designation "Cytodex 2" by Pharmacia AB, Sweden. They have a charge capacity of from 0.5 to 0.8 meq/g.

However, in spite of this further reduced charge capacity, these microcarriers in practice still have displayed disadvantageous effects that are attributed to an adsorption of components of the culture medium to the carrier. Thus, in German Offenlegungsschrift No. 30 33 885, charge-free microcarriers have been described that have been coated with polypeptides such as collagen or gelatin. However, to these microcarriers there can only adhere cells that on the surface thereof contain structural elements that have a sufficient bonding affinity to the polypeptide layer on the microcarrier.

GENERAL DISCUSSION OF THE INVENTION

It is the object of the present invention to provide a cell culture microcarrier comprising positively charged portions of cross-linked polysaccharides and basic groups linked therewith, which do not have any of the aforementioned drawbacks. More specifically, it is the object of the present invention to develop a microcarrier that may be employed even on a commercial scale for the cultivation of sensitive cells and, thus, substantially have no toxicity.

DETAILED DESCRIPTION OF THE INVENTION

Figure 1:
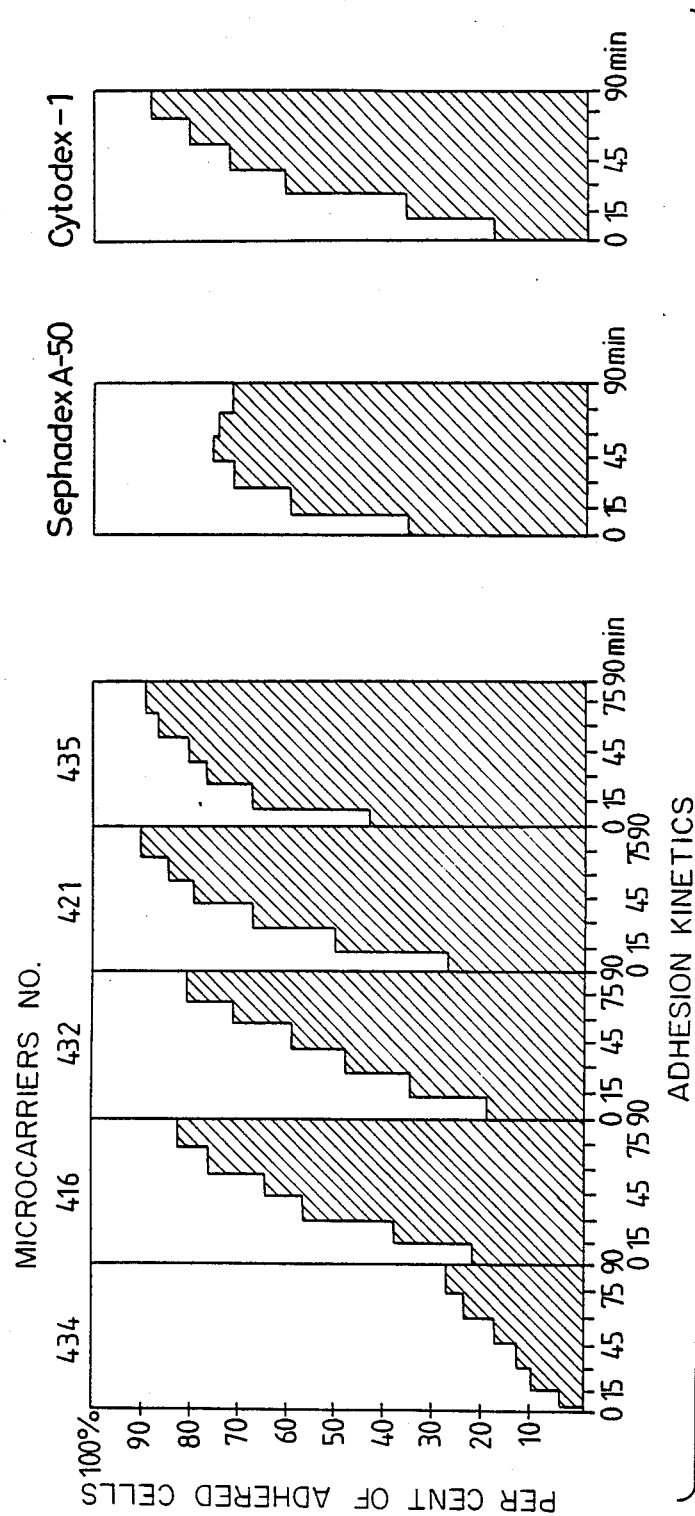
FIG. 1 is a number of plots of percent of adhered cells over time for five microcarriers of the present invention and two prior art microcarriers. The matter is discussed in Example 3, infra.

The object of the present invention, surprisingly, can be attained by providing a polysaccharide with positively charged basic groups of the formula (I)

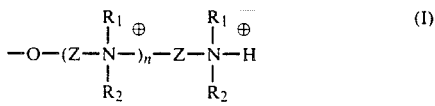

wherein

Z is an optionally substituted hydrocarbon chain having at least 2 carbon atoms, $R_1$ and $R_2$ are the same or different and represent alkyl, aryl, or aralkyl groups, and n is at least 1.

Cell culture microcarriers comprising such positively charged basic groups surprisingly have proven to be not toxic, although the art presumed that such groups would be particularly toxic and, therefore, if possible, should not be present at all or only in a small number on the cell culture microcarriers. Unexpectedly, these positively charged basic groups may even be present in a large number, so that it is not necessary to limit the value of the meq/g of dry cross-linked polysaccharides. One reason for the surprisingly good properties of the cell culture microcarrier of the present invention appears to reside in that it is not the charge density which is of crucial importance, but the pKs value of the positively charged basic groups. While the pKs value of the basic groups of DEAE Sephadex is about 9.2, the pKs values of the cell culture microcarrier according to the invention are in the range of from 5 to 8. A preferred, and readily preparable, cell culture microcarrier of the invention is a polysaccharide containing positively charged basic groups of formula (I) wherein Z is an ethylene group, $R_1$ and $R_2$ represent ethyl, and n is equal to 1; the pKs value is 6.2. Such a cell culture microcarrier is substituted virtually with tandem groups only.

In addition to the mentioned simplest case of tandem groups, according to the invention there may be also used such groups wherein Z contains 3, 4 or more carbon atoms, and wherein $R_1$ and $R_2$, in addition to the ethyl group, also represent methyl groups, propyl groups, isopropyl groups and butyl groups. Since the pKs values will still be in the range of from 5 to 8, $R_1$ and $R_2$ may also be aryl groups such as phenyl and toluyl groups and aralkyl groups such as, more specifically, benzyl groups. Since the pKs values are in the range of from 5 to 8, n may also be larger than 1, so that basic groups comprising 3 or 4 amino groups may also be employed.

As the negative counterions to the positively charged nitrogen atoms, basically all physiologically compatible inorganic and organic anions may be used. Suitable are, more particularly, chloride, phosphate, sulfate and acetate ions.

The pKs values of the basic substituents may be readily determined by titration. The titration curves show the known point of inflexion at the pKs value.

The present invention further relates to a method of preparing the new cell culture microcarrier. The preparation is accomplished by the per se known reaction of a cross-linked polysaccharide with a compound of the formula (II)

wherein

Z is an optionally substituted hydrocarbon chain having at least 2 carbon atoms, $R_1$ and $R_2$ are the same or different and represent alkyl, aryl or aralkyl groups and Y is a reactive group.

The reactive group, more specifically, may be chloride, bromide, but also a sulfonic acid group etc., which is capable of effecting an O-alkylation of the cross-linked polysaccharide.

According to the invention the reaction is carried out in the presence of a strong base in at least two steps and using at least a two times molar excess of compound (II). It is preferred that the aqueous alkaline suspension of the cross-linked polysaccharide is poured into a suspension medium such as toluene, paraffins, water, and reacted with compound (II) while stirring. Subsequently it is preferred that the positively charged basic groups are neutralized by physiologically compatible anions.

As the cross-linked polysaccharides, there may preferably be used the known cross-linked polydextrans. However, basically any other swellable and cross-linked polysaccharide may also be used as the carrier of the positive basic groups.

The new cell culture microcarrier, a method for preparing same and the use thereof are further illustrated by way of the following examples, although the present invention is not limited thereto.

EXAMPLE 1

Preparation of the microcarrier

Dry cross-linked dextran beads (Polydex PL-50 or Sephadex G 50) having a water absorption of about 5 g/g and a particle size of from 80 to 100 μm (13 g) are allowed to swell in distilled water overnight. After removal by suction of the excess water the swelled beads are admixed with 5.3 g of a 43% by weight sodium hydroxide solution. The thus-prepared alkaline suspension of dextran beads is poured into 120 g of toluene pre-warmed to 50° C. Then, 8 ml of chloroethyl-diethylamine are added to the reaction mixture with vigorous stirring. After a reaction period of 3 hours at 50° C., a further 10 ml of chloroethyl-diethylamine are added.

The reaction is completed after another 3 hours of stirring at 50° C. The reacted dextran beads are separated from the reaction mixture by filtration. The microcarriers are purified by washing several times with alcohol and distilled water and adjusting the pH to 5.0 using diluted hydrochloric acid. De-swelling is eventually effected by repeated treatment of the beads with washing solutions having increasing alcohol concentrations. The de-swelled beads are dried at 80° C. overnight.

The microcarriers prepared in accordance with the described method contain about 4.0% of nitrogen and have a charge capacity of 2.86 meq/g of the microcarrier and 4.66 meq/g of the dry untreated dextran, respectively.

The exchange capacity of the thus prepared microcarriers is 2.4 meq/g of the microcarrier and 3.91 meq/g of the dry untreated cross-linked dextran, respectively.

For the determination of the exchange capacity, 1.0 g of the dried microcarriers is allowed to swell in distilled water, transferred to a small column, and washed with 0.1 N diluted hydrochloric acid several times. The removal of the non-bonded chloride ions is accomplished by rinsing the beads with $10^{-4}$ N hydrochloric acid.

The bonded chloride ions are displaced by the addition of a sufficient amount of 10% sodium sulfate solution and then determined by titrating the eluate with 0.1 N silver nitrate solution with potassium chromate as indicator.

The obtained result indicates the number of milliequivalents of $Cl^-$ per gram of the microcarrier. The calculation of the milliequivalents of $Cl^-$ per gram of the untreated dextran beads is made using the following formula:

$$1,000 \times \frac{\text{meq } Cl^-/g \text{ microcarrier}}{1,000 - 135 \times \frac{\% N \times 1,000}{100 \times 14}}$$

The determination of the structure of the thus-bound nitrogen compounds is effected by titration of 1 g of the dry microcarrier in 20 ml of a 1 M potassium chloride solution after adjustment of the initial pH to 12 using 1 N hydrochloric acid. The titration curve reveals, by the absence of a step in the pH range of from 10 to 8.5, that tertiary amino groups are no longer present. The pKs value of the amino compound is between 5 and 7.

EXAMPLE 2

By way of variation of the used amounts of sodium hydroxide solution and chloroethyldiethylamine, the following microcarriers No. 434, 416, 432, and 435 are prepared.

| Microcarrier No. | Polydex PL 50 g | NaOH g | Choloroethyl-diethylamine (1) ml | (2) ml |
|---|---|---|---|---|
| 434 | 9.5 | 0.275 | 1.0 | 1.25 |
| 416 | 4.0 | | 0.22 | 0.8 | 1.0 |
| 432 | 13.0 | | 2.1 | 7.8 | 9.5 |
| 421 | 13.0 | | 2.2 | 8.0 | 10.0 |
| 435 | 9.5 | | 3.76 | 13.0 | 16.5 |

| Substance | % N | A | B | C | D |
|---|---|---|---|---|---|
| 434 | 1.0 | 0.66 | 0.71 | 0.73 | 0.79 |
| 416 | 1.8 | 1.14 | 1.29 | 1.38 | 1.56 |
| 432 | 3.8 | 2.33 | 2.71 | 3.68 | 4.27 |
| 421 | 4.0 | 2.4 | 2.86 | 3.91 | 4.66 |
| 435 | 4.8 | 3.0 | 3.43 | 5.59 | 6.39 |
| Sephadex A-50 | 4.2 | 2.7 | 3.0 | 4.54 | 5.04 |
| Cytodex 1 | 1.8 | 1.2 | 1.29 | 1.45 | 1.56 |

Notes:
A: Exchange capacity per gram of microcarrier;
B: Charge capacity per gram of microcarrier;
C: Exchange capacity per gram of untreated cross-linked dextran;
D: Charge capacity per gram of untreated cross-linked dextran.

EXAMPLE 3

Kinetics of adhesion of GMK (Green Monkey Kidney) cells

Microcarriers, prepared as in Examples 1 or 2, respectively, each in a quantity of 5 mg/ml were incubated in Petri dishes for bacteriological use having a diameter of 6 cm with 5 ml of medium MEM (Minimum Essential Medium) and 8% of FBS (Fetal Bovine Serum) at 37° C. for 1 hour.

After the addition of fresh GMK cells stripped in trypsin/versene so that a concentration of $2.6 \times 10^5$ cells/ml of medium was obtained, samples were taken every 15 minutes. The degree of adhesion can be determined by counting the non-bonded cells.

In comparison to the cell carrier materials according to the invention, the adhesion kinetics were also determined using the commercially available microcarriers based on dextran (Cytodex ®) having a charge density of 2.0 meq/g of neutral dextran matrix and using the anion exchanger Sephadex A-50 ®.

The results as presented in FIG. 1 show that the new microcarriers are not toxic even with a high charge capacity, whereas Sephadex A-50 displays the known toxic effects after about 50 minutes.

EXAMPLE 4

Growth of anchorage-dependent cells, exemplified by GMK cells on the microcarriers No. 416 and 421 having different charge densities.

Each of the dried microcarriers in a quantity of 0.3 g was allowed to swell in 20 ml of PBS and then sterilized at 115° C. under 15 psi for 15 minutes.

The PBS is decanted and replaced by warm culture medium. For example, MEM (Minimum Essential Medium) with an addition of 8% of Fetal Bovine Serum (FBS) serves as the culture medium. The bead suspensions transferred into culture vessels, and preferably into special spinner flasks. The volume was replenished with the culture medium+8% of FBS to 100 ml, and then gas was passed into the batch, and the temperature was adjusted. Inoculation was effected with a cell inoculum of $1.3 \times 10^7$ GMK (Green Monkey Kidney) cells originating from passage No. 127 of the Institut für Virologie of the University of Cologne, West Germany, and had been pre-cultivated in plastic flasks containing culture medium for 5 days.

Figure 2:
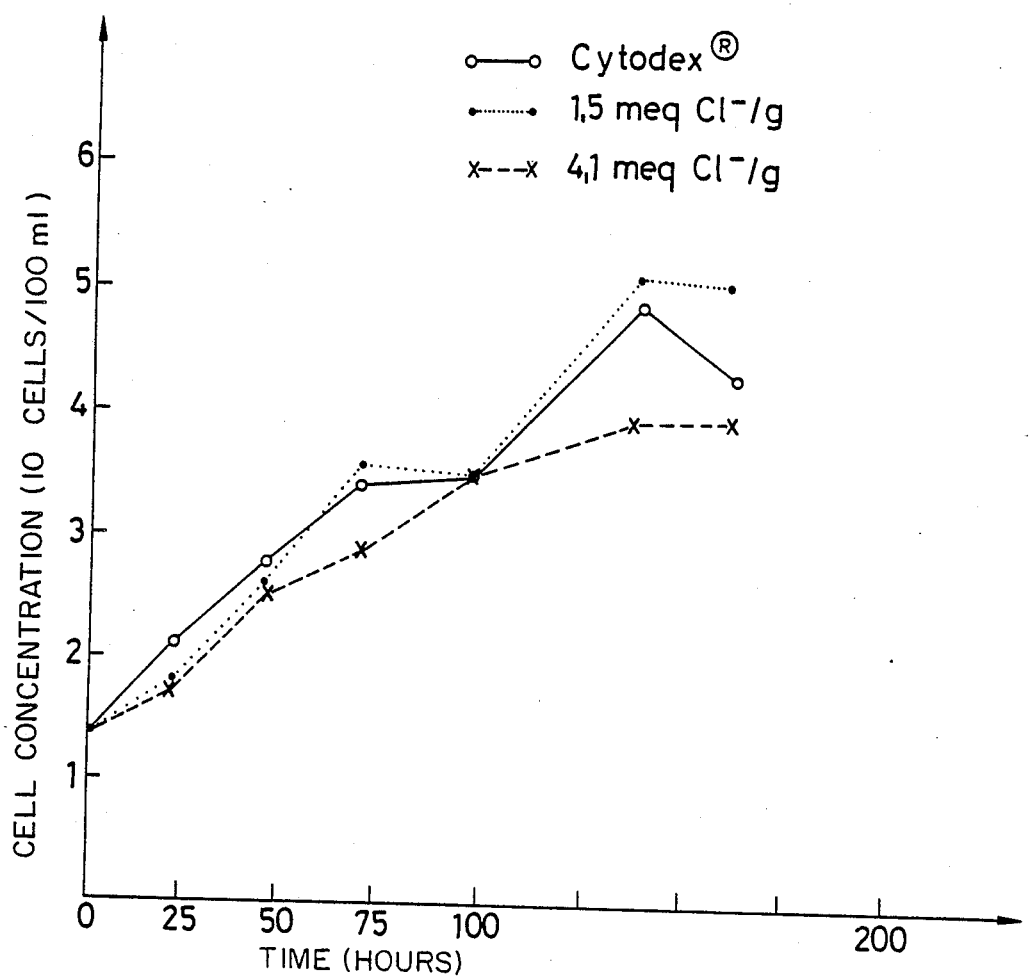
FIG. 2 is a plot of cell concentration over time for two microcarriers of the present invention and one prior art microcarrier; see Example 4, infra.

After an initial static phase of adhesion, a stirring speed of 30 rpm was adjusted. The medium was changed every 48 hours. The cell growth was monitored through a period of 170 hours by removing the cells from the carriers by trypsinating and counting them in accordance with a modified Sanfort et al. method (J. Natl. Cancer Inst. II, 737 (1951)). For comparison, the growth on the known Cytodex 1 microcarriers was determined at the same time. The result is seen from FIG. 2. It is apparent from FIG. 2 that the growth on the new microcarriers is good even at a high charge capacity.

What is claimed is:

1. Process for cultivating anchorage-dependent cells in a microcarrier culture comprising cultivating anchorage-dependent cells with a cell culture microcarrier having a pK of 5–8 and comprising positively charged cross-linked polysaccharides and positively charged basic groups linked therewith, said positively charged basic groups having the formula (I)

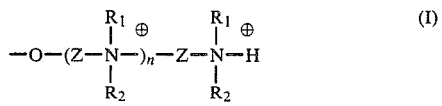

wherein

Z is a hydrocarbon chain having 2 to about 5 carbon atoms, $R_1$ and $R_2$ are the same or different and represent $C_{1-4}$ alkyl groups, and n is 1 to about 4.

2. Process of claim 1 wherein Z is an ethylene group, $R_1$ and $R_2$ each represent an ethyl group and n is 1.

3. Process of claim 1 wherein said positively charged basic groups have been neutralized by physiologically compatible anions.

4. Process of claim 2 wherein said positively charged basic groups have been neutralized by physiologically compatible anions.

* * * * *